(12) United States Patent
Bottke et al.

(10) Patent No.: US 7,601,861 B2
(45) Date of Patent: Oct. 13, 2009

(54) METHOD FOR PRODUCING ALKYLARYL COMPOUNDS AND ALKYLARYL SULPHONATES

(75) Inventors: Nils Bottke, Mannheim (DE); Regina Benfer, Altrip (DE); Marco Bosch, Mannheim (DE); Thomas Narbeshuber, Mannheim (DE); Ulrich Steinbrenner, Neustadt (DE); Juergen Stephan, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 76 days.

(21) Appl. No.: 10/577,321

(22) PCT Filed: Oct. 29, 2004

(86) PCT No.: PCT/EP2004/012280

§ 371 (c)(1),
(2), (4) Date: Apr. 28, 2006

(87) PCT Pub. No.: WO2005/042448

PCT Pub. Date: May 12, 2005

(65) Prior Publication Data

US 2007/0078075 A1    Apr. 5, 2007

(30) Foreign Application Priority Data

Oct. 29, 2003  (DE) ............................... 103 50 333

(51) Int. Cl.
*C07C 309/31* (2006.01)

(52) U.S. Cl. .................. 558/56; 585/455; 585/456
(58) Field of Classification Search ................ 585/455, 585/456; 558/56
See application file for complete search history.

(56) References Cited

FOREIGN PATENT DOCUMENTS

| DE | 100 39 995 |   | 2/2002 |
| DE | 100 59 398 |   | 6/2002 |
| WO | 99/05244 | * | 2/1999 |
| WO | 02/092737 | * | 11/2002 |
| WO | 03/029172 |   | 4/2003 |

OTHER PUBLICATIONS

Wang, Honglin et al., "Surface acidity of H-beta and its catalytic activity for alkylation of benzene with propylene", Catalysis Letters, vol. 76, No. 3-4, pp. 225-229, 2001.

* cited by examiner

*Primary Examiner*—Peter G O'Sullivan
(74) *Attorney, Agent, or Firm*—Oblon, Spivak, McClelland, Maier & Neustadt, L.L.P.

(57) ABSTRACT

In a process for preparing alkylaryl compounds by reacting a $C_{10-14}$-monoolefin mixture with an aromatic hydrocarbon in the presence of an alkylation catalyst to form alkyl aromatic compounds and if appropriate subsequently sulfonating and neutralizing the resulting alkylaryl compounds, in the $C_{10-14}$-monoolefins, on average, more than 0% and up to 100% of methyl branches are present in the longest carbon chain and fewer than 50% of the methyl branches are in the 2-, 3- and 4-position, calculated starting from the chain ends of the longest carbon chain.

12 Claims, No Drawings

METHOD FOR PRODUCING ALKYLARYL COMPOUNDS AND ALKYLARYL SULPHONATES

The present invention relates to processes for preparing alkylaryl compounds and alkylarylsulfonates, to alkylaryls and alkylarylsulfonates obtainable by these processes, to the use of the latter as surfactants, preferably in laundry detergents and cleaning compositions, and to laundry detergents and cleaning compositions comprising them.

Alkylbenzenesulfonates (ABS) have been used for some time as surfactants in laundry detergents and cleaning compositions. After such surfactants based on tetrapropylenebenzenesulfonate had been used at first, but had poor biodegradability, substantially linear alkylbenzenesulfonates (LAS) were prepared and used in the subsequent time. However, linear alkylbenzenesulfonates do not have adequate property profiles in all fields of application.

It would be advantageous, for example, to improve their cold-wash properties or their properties in hard water. Likewise desirable is ease of formulation, arising from the viscosity of the sulfonates and their solubility. These improved properties are exhibited by slightly branched compounds or mixtures of slightly branched compounds with linear compounds, although the correct degree of branching and/or the correct degree of mixing have to be achieved. Excessive branching impairs the biodegradability of the products. Excessively linear products have a negative influence on the viscosity and the solubility of the sulfonates.

Moreover, the ratio of terminal phenylalkanes (2-phenylalkanes and 3-phenylalkanes) to internal phenylalkanes (4-, 5-, 6-, etc., phenylalkanes) plays a role in the product properties. A 2-phenyl fraction of about 20-40% and a 2- and 3-phenyl fraction of about 40-60% may be advantageous with regard to the product quality (solubility, viscosity, wash properties, biodegradability).

To prepare slightly branched alkylbenzenes (MLAB), for example, a slightly branched olefin mixture is reacted with benzene in the presence of an alkylation catalyst. The position of the phenyl group is determined by the shape selectivity of the catalyst. Zeolites of the mordenite structure type react with approx. 85% preference to give 2-phenylalkenes; approx. 15% of 3-phenylalkane is formed, see Wang et al. *Catal. Letters* 2001, 76, 1-2.

Surfactants having very high 2- and 3-phenyl contents may have the crucial disadvantage that the processibility of the products suffers by a large rise in the viscosity of the sulfonates.

Moreover, imperfect dissolution behavior may result. For instance, the Krafft point of a solution of LAS having very high or very low 2- and 3-phenyl fractions is up to 10-20° C. higher than when the optimum 2- and 3-phenyl fraction is selected.

WO 03/029172 describes processes for preparing alkylaryl compounds in which $C_4$ olefin mixtures stemming from LPG, LNG or MTO streams are converted to $C_{10-12}$-olefins by metathesis and dimerization, and are then used to alkylate aromatic hydrocarbons. The process provides semibranched alkylaryl compounds which are said to have advantageous properties when used as surfactants.

DE-A-100 39 995 relates to processes for preparing alkylarylsulfonates which are obtained by a two-stage metathesis of $C_4$ olefins to $C_{10-12}$-olefins, followed by alkylation of aromatic compounds, and subsequent sulfonation and neutralization. The sources listed for the $C_4$ olefins are crack processes such as steamcracking or FCC cracking or the dehydrogenation of butanes or the dimerization of ethene. In the latter processes, dienes, alkynes or enynes may be removed before the metathesis by common methods such as extraction or selective hydrogenation.

DE-A-100 59 398 likewise relates to a process for preparing alkylarylsulfonates in which, on statistical average, predominantly monobranched $C_{10-14}$-olefins are reacted with an aromatic hydrocarbon in the presence of an alkylation catalyst which contains zeolites of the faujasite type. The $C_{10-14}$-olefins may be obtained by metathesis, extraction, Fischer-Tropsch synthesis, dimerization or isomerization.

Some of the olefins used hitherto for alkylation have too high or too low a degree of branching or have an imperfect ratio of terminal to internal phenylalkanes.

It is an object of the present invention to provide a process for preparing alkylaryl compounds and alkylarylsulfonates which are at least partly branched and thus have advantageous properties for use in laundry detergents and cleaning compositions compared to the known compounds. They should in particular have a suitable property profile of biodegradability, insensitivity to water hardness, solubility and viscosity in the course of the preparation and in the course of use. In addition, it should be possible to prepare the alkylarylsulfonates inexpensively.

According to the invention, this object is achieved by a process for preparing alkylaryl compounds by reacting a $C_{10-14}$-monoolefin mixture with an aromatic hydrocarbon in the presence of an alkylation catalyst to form alkyl aromatic compounds and if appropriate subsequently sulfonating and neutralizing the resulting alkylaryl compounds, wherein, in the $C_{10-14}$-monoolefins, on average, more than 0% and up to 100% of methyl branches are present in the longest carbon chain and fewer than 50% of the methyl branches are in the 2-, 3- and 4-position, calculated starting from the chain ends of the longest carbon chain.

The process according to the invention offers the significant advantage that the use of the unique olefin mixture, after alkylation of an aromatic, sulfonation and neutralization, affords a surfactant which features a combination of excellent performance properties (solubility, viscosity, stability toward water hardness, wash properties, biodegradability). With regard to the biodegradability of alkylarylsulfonates, compounds which are less strongly adsorbed on sewage sludge than the conventional LAS are particularly advantageous.

In the alkylation step, there is skeletal isomerization of the olefin, for example alkyl group migration. The branch structure of the olefin mixture used differs from that in the side chain of the MLAB isomers formed, i.e. type and position of the branches may be changed in the alkylation. However, the degree of branching is very substantially retained.

According to the invention, it has been found that, for the preparation of slightly branched alkylbenzenes (MLAB), it is not only the proportion of singly methyl-branched olefin and therefore the degree of branching that is important in the alkylation, but rather equally the position of the methyl groups. The substantial, preferably complete, absence of 2-, 3- and 4-methyl branches in the starting olefin has been found to be particularly favorable for the product quality of the MLAB, and also for the lifetime of the alkylation catalyst.

In this context, it is unimportant where the double bond is in the olefin, since it is isomerized under the conditions of the alkylation. In the context of this application, and in a departure from the IUPAC rules, "methyl branch in the 2-position", for example, is intended to refer to all alkenes which, after hydrogenation, are converted to alkanes which, according to the IUPAC rules (reference: for example, "Hellwinkel"), belong to the 2-methylalkanes. For example, 2-methylundec-2-ene is to be equated with 10-methylundec-2-ene, but also with, for example, 10-methylundec-4-ene. The same applies to the methyl branches in the 3- and 4-position along or in the longest carbon chain. In the case of the reaction of methylalkanes with benzene in the presence of an alkylation catalyst, skeletal rearrangement only occurs to a slight extent. The quaternary alkylbenzenes, 2-methyl-2-phenylalkane and 3-methyl-3-phenylalkane, are formed predominantly.

It is known that the structures of this type have only poor biodegradability and their presence therefore reduces the product quality; cf. WO 99/05244 and WO 02/092737.

The use of 4-methylalkenes (alkene having an alkyl radical in the 4-position, viewed from one end of the longest carbon chain) in the alkylation leads to a rapid deactivation of the catalyst. The formation of bulky 4-methyl-4-phenylalkanes may lead to blockage of the channels or coverage of the active centers of the catalyst.

According to the invention, it has been found that both the reaction of 5-methylalkenes and 6-methylalkenes (i.e. alkenes having methyl radicals in the 5- or 6-position, viewed from the chain ends of the longest carbon chain) with benzene in the presence of the same alkylation catalyst forms alkylbenzenes having predominantly singly methyl-branched side chains. The lifetime of the catalyst is high, the fraction of quaternary MLAB low, although methyl group migration forms isomers in which the methyl group is in the 2-, 3- or 4-position of the side chain.

According to the invention, $C_{10-14}$-monoolefin mixtures are used. These may be mixtures of $C_{10}$-, $C_{11}$-, $C_{12}$-, $C_{13}$- or $C_{14}$-monoolefins or else be mixtures of monoolefins having different chain length. For example, $C_{10-12}$-monoolefins having chain lengths in this range may be used. Typically, each of the chain lengths is a mixture of branched and unbranched olefins, and the branched olefins in turn are differently branched olefins.

According to the invention, on average in the $C_{10-14}$-monoolefins, more than 0% and up to 100%, preferably from 10% to 80%, more preferably from 10% to 60%, of methyl branches are present in the longest carbon chain, and fewer than 50%, preferably fewer than 30%, more preferably fewer than 10%, in particular fewer than 5%, of the methyl branches are present in the 2-, 3- and 4-position, calculated starting from the chain ends of the longest carbon chain. The 2-, 3- and 4-position relate to the longest carbon chain irrespective of the position of the double bond within the carbon chain. The term "on average" means that, for example, in the case of 100% methyl branches, each olefin chain statistically has one methyl branch, although there may in practice be olefins present in the mixture which have no, one, two or more methyl branches. The $C_{10-14}$-monoolefins in each case preferably have a maximum of 2 methyl branches, in particular a maximum of one methyl branch.

The fraction and the position of the methyl branches may be determined by gas chromatography and by the customary methods.

The olefin mixture may stem from a multitude of sources and if appropriate be aftertreated by suitable steps in order to exhibit the inventive branching pattern. For example, linear or selectively branched olefins may be added to a mixture, or a removal of certain olefins from the mixture may be carried out.

For example, the olefin is obtained by
a1) preparing a $C_4/C_5$-olefin mixture,
b1) converting the $C_4/C_5$-olefin mixture obtained in this way over a metathesis catalyst to prepare an olefin mixture comprising 2-pentene and/or 3-hexene and/or 3-heptene, and if appropriate removing 2-pentene and/or 3-hexene and/or 3-heptene,
c1) dimerizing the 2-pentene and/or 3-hexene and/or 3-heptene obtained in stage b1) over a dimerization catalyst to give a mixture comprising $C_{10-14}$-olefins and if appropriate removing the $C_{10-14}$-olefins.

In stage a1), the $C_4$-olefins of the $C_4/C_5$-olefin mixture may be obtained by dehydrogenating the $C_4$ fraction of the LPG, LNG or MTO stream and subsequently removing any dienes, alkynes and enynes formed, and the $C_4$ fraction of the LPG, LNG or MTO stream may be removed from the LPG, LNG or MTO stream before or after the dehydrogenation and removal of dienes, alkynes and enynes. The LNG stream may be converted to the $C_4$-olefin mixture via an MTO process.

In stage c1), heptenes may also be mixed in.

The olefin mixture may also be obtained by
a2) preparing a $C_{5-7}$-olefin mixture by dehydrogenating $C_{5-7}$-alkanes with upstream or downstream isomerization if appropriate,
b2) dimerizing the $C_{5-7}$-olefin mixture obtained in stage a2) over a dimerization catalyst to give a mixture comprising $C_{10-14}$-olefins and if appropriate removing the $C_{10-14}$-olefins.

Suitable aromatics are benzene, toluene, ethylbenzene and the xylenes; preference is given to benzene, toluene and ethylbenzene, particular preference to benzene.

Suitable catalysts are zeolites of the EPI, FER structure types, pentasils having MFI or MEL structure, faujasites, for example Y, LTL, MOR, BEA, GME, MAZ. Preference is given to LTL, FAU including the USY types, BEA and MOR. Particular preference is given to MOR.

These zeolites are preferably used in the H and/or Al form, although, depending on the preparation, traces of Na, K, Mg or Ca may be present. Partial or full exchange of the lattice aluminum for B, Ga or Fe is possible.

The catalyst may be used directly as a fine powder in suspension; in the case of zeolites, these are, for example, particle sizes between 100 nm and a few μm. However, these catalysts are usually shaped together with binder materials to give shaped bodies of diameter 0.1-5 mm. For use in fixed beds, preference is given to 1-3 mm, to 0.001-1 mm in suspension, to 0.1-3 mm in fluidized beds. Particularly suitable binders are clays, aluminas, for example Purals, Sirals and Versals, and silica gels. In addition, inert fillers such as $SiO_2$ (for example Aerosil from Degussa) may be added.

Suitable shaped bodies are tablets, extrudates, rings, ribbed extrudates, star or wagonwheel extrudates.

The catalysts preferably have specific surface areas of from 30 to 2000 $m^2/g$, preferably from 100 to 700 $m^2/g$. The volume of the pores having diameter 2-20 nm is typically 0.05-0.5 ml/g, preferably from 0.01 to 0.1 ml/g, and that of the pores of 200-2000 nm typically 0.05-0.5 ml/g, preferably from 0.05 to 0.3 ml/g.

Deactivated catalysts can in most cases be reactivated, for example, by burning-off in air or lean air at 250-550° C. Alternatively, treatment with compounds having oxidizing action at relatively low temperature, optionally also in the liquid phase, is possible; mention should be made here in particular of $NO_x$, $H_2O_2$ and the halogens. The regeneration may be effected directly in the alkylation reactor or externally.

The alkylation preferably takes place in the liquid phase, i.e. without gas phase, which may be achieved by an appropriate system pressure. Alkylation temperatures are preferably from 100 to 250° C., more preferably from 120 to 220° C., even more preferably from 130 to 220° C., especially from 150° C. to 180° C., for example 160° C.

Suitable reactors are, for example, all systems having stirred tank characteristics, i.e. stirred tanks, loop reactors, reactors having external circulation, jet loop reactors, and also fluidized or moving beds are suitable.

The invention also relates to alkylaryl compounds, especially alkylbenzenesulfonates, which are obtainable by the process according to the invention. The alkylbenzenesulfonates may preferably be used as surfactants, especially in laundry detergents and cleaning compositions.

The invention also relates to laundry detergents and cleaning compositions which comprise the inventive alkylbenzenesulfonates in addition to customary ingredients. For customary ingredients and laundry detergent compositions, reference may be made to WO 03/029172. There, customary ingredients such as bleaches, bleach activators, bleach stabilizers, inorganic builders (builder substances), anionic surfactants, nonionic surfactants, organic cobuilders, graying inhibitors and soil release polymers, color transfer inhibitors, enzymes, etc., are listed.

A typical inventive pulverulent or granular heavy-duty laundry detergent may have, for example, the following composition:

from 0.5 to 50% by weight, preferably from 5 to 30% by weight, of at least one anionic and/or nonionic surfactant, from 0.5 to 60% by weight, preferably from 15 to 40% by weight, of at least one inorganic builder, from 0 to 20% by weight, preferably from 0.5 to 8% by weight, of at least one organic cobuilder, from 2 to 35% by weight, preferably from 5 to 30% by weight, of an inorganic bleach, from 0.1 to 20% by weight, preferably from 0.5 to 10% by weight, of a bleach activator, if appropriate in a mixture with further bleach activators, from 0 to 1% by weight, preferably up to at most 0.5% by weight, of a bleach catalyst, from 0 to 5% by weight, preferably from 0 to 2.5% by weight, of a polymeric color transfer inhibitor, from 0 to 1.5% by weight, preferably from 0.1 to 1.0% by weight, of proteases, from 0 to 1.5% by weight, preferably from 0.1 to 1.0% by weight, of lipases, from 0 to 1.5% by weight, preferably from 0.2 to 1.0% by weight, of a soil release polymer, ad 100%, customary assistants and adjuvants and water.

Inorganic builders used with preference in laundry detergents are sodium carbonate, sodium hydrogencarbonate, zeolite A and P, and also amorphous and crystalline sodium silicates.

Organic cobuilders used with preference in laundry detergents are acrylic acid/maleic acid copolymers, acrylic acid/maleic acid/vinyl ester terpolymers and citric acid.

Inorganic bleaches used with preference in laundry detergents are sodium perborate and sodium carbonate perhydrate.

Anionic surfactants used with preference in laundry detergents are the inventive linear and slightly branched alkylbenzenesulfonates (LAS), fatty alcohol sulfates and soaps.

Nonionic surfactants used with preference in laundry detergents are $C_{11}$ to $C_{17}$ oxo alcohol ethoxylates having 3-13 ethylene oxide units, $C_{10}$ to $C_{16}$ fatty alcohol ethoxylates having 3-13 ethylene oxide units, and also ethoxylated fatty or oxo alcohols additionally alkoxylated with 1-4 propylene oxide or butylene oxide units.

Enzymes used with preference in laundry detergents are proteases, lipases and cellulases. The commercial enzymes are added to the laundry detergent generally in amounts of from 0.05 to 2.0% by weight, preferably from 0.2 to 1.5% by weight, of the formulated enzyme. Suitable proteases are, for example, Savinase, Desazym and Esperase (manufacturer: Novo Nordisk). A suitable lipase is, for example, Lipolase (manufacturer: Novo Nordisk). A suitable cellulase is, for example, Celluzym (manufacturer: Novo Nordisk).

Graying inhibitors and soil release polymers which are used with preference in laundry detergents are graft polymers of vinyl acetate on polyethylene oxide of molar mass 2500-8000 in a weight ratio of from 1.2:1 to 3.0:1, polyethylene terephthalate/oxyethylene terephthalate of molar mass from 3000 to 25 000 composed of polyethylene oxides of molar mass from 750 to 5000 with terephthalic acid and ethylene oxide and a molar ratio of polyethylene terephthalate to polyoxyethylene terephthalate of from 8:1 to 1:1, and also block polycondensates according to DE-A-44 03 866.

Color transfer inhibitors which are used with preference in laundry detergents are soluble vinylpyrrolidone and vinylimidazole copolymers having molar masses of above 25 000, and also finely divided crosslinked polymers based on vinylimidazole.

The inventive pulverulent or granular laundry detergents may contain up to 60% by weight of inorganic extenders. It is customary to use sodium sulfate for this purpose. However, the inventive laundry detergents are preferably low in extenders and contain only up to 20% by weight, more preferably only up to 8% by weight, of extenders.

The inventive laundry detergents may have varying bulk densities in the range from 300 to 1200 g/l, in particular from 500 to 950 g/l. Modern compact laundry detergents generally have high bulk densities and exhibit a granular structure.

The invention is illustrated with detail with reference to the examples which follow.

EXAMPLES

Example 1

A tubular reactor disposed in a forced-air oven was charged with 32 g of catalyst spall (60% of H-mordenite having $SiO_2$:$Al_2O_3$=24.5, shaped with 40% Pural SB from Condea) of particle size 0.7-1.0 mm, and activated at 500° C. for 6 h. The oven was then cooled, flooded with a feed of benzene: 5-methylundecene (4:1 molar) and charged at 0.44 $g/g_{cat}h$, and the flow rate of the circulation stream was set ten times higher. Finally, the reactor was heated to 160° C. (monophasic liquid, 30 bar of hydraulic pressure), and the content of reactants and products in the effluent stream was detected by means of time-resolved GC. The resulting $C_{18}$-alkylaryl mixture was purified by distillation and analyzed by means of gas chromatography-mass spectrometry coupling and $^{1}H/^{13}C$ NMR. After 86 hours, a reduction in the dodecene conversion to below 95% was observed.

Example 2 (Comparative)

In the apparatus from example 1, a feed of benzene: 4-methylundecene (4:1 molar) was converted under similar conditions. The reduction in the dodecene conversion to below 95% was observed as early as after 30 hours.

Example 3

In an autoclave, different methylundecenes as specified below were reacted with benzene in a molar ratio of 1:10 at different temperatures over a mordenite catalyst (5% by weight). The results are summarized in the tables which follow:

Conversion of 2-methylundecene (Comparative)

| Reaction temperature | Reaction products | |
|---|---|---|
| | 2-m-2-p | 3-m-3-p |
| 100° C. | 100% | <1% |
| 120° C. | 94.9% | <1% |
| 140° C. | 88.7% | <1% |
| 160° C. | 86.9% | <1% |
| 180° C. | 77.8% | <1% |
| 200° C. | 42.5% | <1% |

Conversion of 3-methylundecene (Comparative)

| Reaction temperature | Reaction products | | |
|---|---|---|---|
| | 2-m-2-p | 3-m-2-p | 3-m-3-p |
| 100° C. | 13.6% | 47.4% | 15.6% |
| 120° C. | 16.1% | 50.4% | 12.7% |
| 140° C. | 14.4% | 46.6% | 8.9% |
| 160° C. | 13.8% | 44.0% | 6.3% |
| 180° C. | 19.3% | 39.8% | 8.0% |
| 200° C. | 21.9% | 27.4% | 4.7% |

Conversion of 5-methylundecene

| Reaction temperature | Reaction products | | |
|---|---|---|---|
| | 5/7-m-2-p | 2-m-2-p | 3-m-3-p |
| 100° C. | 47.9% | 1.6% | <1% |
| 120° C. | 50.0% | 2.2% | <1% |
| 140° C. | 47.6% | 3.2% | <1% |
| 160° C. | 47.5% | 2.1% | <1% |
| 180° C. | 30.3% | 2.9% | <1% |
| 200° C. | 23.3% | 2.0% | <1% |

Conversion of 6-methylundecene

| Reaction temperature | Reaction products | | |
|---|---|---|---|
| | 6-m-2-p | 2-m-2-p | 3-m-3-p |
| 160° C. | 48.0 | 1.8% | <1% |
| 180° C. | 40.7 | 3.2% | <1% |

In the abbreviations for the products, m means methyl and p phenylundecane. 2-m-2-p thus means 2-methyl-2-phenylundecane.

Example 4 (Comparative)

In WO 01/05733 A1 (UOP), the composition of an olefin ex isomerization/dehydrogenation is specified as follows:

| Olefin | Content |
|---|---|
| Light olefins | 0.64% |
| Linear olefins | 30.11% |
| 6-Methylundecene | 7.66% |
| 5-Methylundecene | 15.33% |
| 4-Methylundecene | 11.82% |
| 3-Methylundecene | 12.95% |
| 2-Methylundecene | 8.87% |
| Other branched olefins | 9.05% |
| Higher isomers | 3.53% |
| Sum | 99.96% |

A mixture of this olefin with benzene (93.3% benzene, 6.7% olefin, molar benzene:olefin ratio approx. 30:1) was converted at 125° C. and 35 bar in the presence of 75 ml (53.0 g) of mordenite at an LHSV of 2.0 h$^{-1}$ (hourly space velocity of 0.15 g of olefin/g of cat.).

The 2-phenyl selectivity in the product was determined to be 82.0%, the fraction of 2-methyl-2-phenylundecane 6.98% and the fraction of higher quarts 1.9%.

Example 5

Under the conditions specified above in example 4, an olefin from the olefin hydroformylation-aldol condensation-hydrogenation-dehydration chain or according to example 3 of WO 03/029172 was used.

| Olefin | Content |
|---|---|
| Linear olefins | 14.0% |
| 5-Methylundecene | 35.0% |
| 4-Ethyldecene | 32.5% |
| More highly branched olefins | 17.0% |
| Higher isomers | 1.4% |
| Sum | 99.9% |

The 2-phenyl selectivity in the product was determined to be 82.4%, the fraction of 2-methyl-2-phenylundecane 2.33% and the fraction of higher quarts 0.8%.

We claim:

1. A process for preparing at least one alkylaryl compound comprising:
   reacting a $C_{10-14}$-monoolefin mixture with an aromatic hydrocarbon in the presence of an alkylation catalyst to form at least one alkyl aromatic compound;
   wherein, in the $C_{10-14}$-monoolefins, on average, more than 0% and up to 100% of methyl branches are present in the longest carbon chain and fewer than 30% of the methyl branches are in the 2-, 3- and 4-position, calculated starting from the chain ends of the longest carbon chain; and
   the alkylation catalyst is selected from the group consisting of a zeolite of the EPI structural type, a zeolite of the FER structural type, a pentasil having an MFI structure, and a pentasil having an MEL structure.

2. A process according to claim 1, wherein, in the $C_{10-14}$-monoolefins, on average, from 10 to 80% of methyl branches are present in the longest hydrocarbon chain.

3. A process according to claim 1, wherein the $C_{10-14}$-monoolefins in each case have a maximum of two methyl branches.

4. A process according to claim 3, wherein the $C_{10-14}$-monoolefins in each case have a maximum of one methyl branch.

5. A process according to claim 1, wherein the aromatic hydrocarbon is benzene.

6. A process according to claim 1, wherein the alkylation is carried out in the liquid phase at a temperature in the range from 100 to 250° C.

7. A process for preparing at least one alkylaryl compound comprising:

reacting a $C_{10-14}$-monoolefin mixture with an aromatic hydrocarbon in the presence of an alkylation catalyst to form at least one alkyl aromatic compound; and sulfonating and neutralizing the resulting at least one alkylaryl compound;

wherein, in the $C_{10-14}$-monoolefins, on average, more than 0% and up to 100% of methyl branches are present in the longest carbon chain and fewer than 30% of the methyl branches are in the 2-, 3- and 4-position, calculated starting from the chain ends of the longest carbon chain; and the alkylation catalyst is selected from the group consisting of a zeolite of the EPI structural type, a zeolite of the FER structural type, a pentasil having an MFI structure, and a pentasil having an MEL structure.

8. The process according to claim 7, wherein, in the $C_{10-14}$-monoolefins, on average, from 10 to 80% of methyl branches are present in the longest hydrocarbon chain.

9. The process according to claim 7, wherein the $C_{10-14}$-monoolefins in each case have a maximum of two methyl branches.

10. The process according to claim 7, wherein the $C_{10-14}$-monoolefins in each case have a maximum of one methyl branch.

11. The process according to claim 7, wherein the aromatic hydrocarbon is benzene.

12. The process according to claim 7, wherein the alkylation is carried out in the liquid phase at a temperature in the range from 100 to 250° C.

* * * * *